United States Patent [19]
Foelsch

[11] 3,987,184
[45] Oct. 19, 1976

[54] DIMETHYLOL DIMETHYLHYDANTOIN SOLUTION

[75] Inventor: Donald Henry Foelsch, Williamsport, Pa.

[73] Assignee: Glyco Chemicals, Inc., Greenwich, Conn.

[22] Filed: June 7, 1974

[21] Appl. No.: 477,274

[52] U.S. Cl. .............................. 424/273; 260/309.5
[51] Int. Cl.$^2$ ........................................ C01B 15/02
[58] Field of Search .................. 260/309.5; 424/273

[56] References Cited
UNITED STATES PATENTS

| | | | |
|---|---|---|---|
| 2,764,573 | 9/1956 | Reibnitz et al. | 260/309.7 X |
| 3,209,010 | 9/1965 | Gagliardi et al. | 260/309.7 |
| 3,213,104 | 10/1965 | Cashin et al. | 260/309.5 |

OTHER PUBLICATIONS
Chem. Abstracts, 65:723b.

Primary Examiner—Ethel G. Love

[57] ABSTRACT

Disclosed is (i) an aqueous solution containing from about 45 to 70% of 1,3-dimethylol-5,5-dimethylhydantoin, having from a maximum of 1.25% to no free formaldehyde, with at least 96.5% of its solute being that dimethylol dimethylhydantoin and having pH from about 7.6 to 7, and (ii) the preparation of that solution by admixing formaldehyde and 5,5-dimethylhydantoin in the ratio from about 1.85 to 2.4 mols of formaldehyde per mol of the dimethylhydantoin in water, adjusting the pH with a compatible alkalizing agent to enable conducting the reaction at a pH of at least 7 to about 9, and allowing the reactants to react at a temperature from about 22° to 65° C. and a pH from 9 to 7 for a time sufficient for the formation of the 1,3-dimethylol-5,5-dimethylhydantoin to be substantially completed. The solution is useful as a formaldehyde donor and for a preservative in various pastes, soaps, skin creams and liquid shampoos.

10 Claims, No Drawings

DIMETHYLOL DIMETHYLHYDANTOIN SOLUTION

This invention relates to (i) a method of preparing an aqueous solution of dimethylol-5,5-dimethylhydantoin (hereinafter briefly called dimethylol-DMH) from formaldehyde and 5,5-dimethylhydantoin (hereinafter briefly called DMH) under certain conditions that provide a resulting very low content of free formaldehyde and a very high content of the desired dimethylol-5,5-dimethylhydantoin in the solute (i.e. dissolved content), and (ii) the resulting aqueous solution of dimethylol-DMH.

The shelf-life of certain preparations such as pastes, soaps, skin creams, or liquid shampoos depends on their resistance to microbial spoilage. Formaldehyde, an antimicrobial agent effective against a number of common microorganisms, has been used in aqueous solution, such as of formalin (containing 37% formaldehyde), for that purpose in a formaldehyde concentration of, for example, 0.1 to 0.2% by admixture mostly into soaps, shampoos, and some hair preparations.

However, that in addition to the unpleasant formaldehyde odor manifests other disadvantages. For example, these products can be applied to the skin for only very short periods, the formaldehyde has short life due to its volatility, and provokes irritation of production personnel engaged in incorporating the formaldehyde solution into the various preparations.

These disadvantages were diminished by using the mono-methylol dimethylhydantoin, a white crystalline product containing about 19% bound (but available) formaldehyde, as a formaldehyde donor. This, for example, incorporated at a 0.1 to 1% concentration served as a preservative by releasing formaldehyde slowly over a prolonged period.

The availability of mono-methylol dimethylhydantion provided some advantage over use of some dilution of the commercial 37% aqueous formaldehyde. However, by its containing only about 19% of available formaldehyde, mono-methylol DMH showed an undesirable cost disadvantage in its requirement of one mol of the DMH for providing at most only one mol of available formaldehyde.

Dimethylol-DMH theoretically contains 31.8% of bound (but available) formaldehyde. Japanese patent No. 4709 (1966) discloses preparing dimethylol-DMH by reacting one mole of dimethylhydantoin with from 3 to 5 mols of formaldehyde (as the 37% by weight HCHO aqueous solution) at 80° C. for 25 to 30 minutes with stirring (without a catalyst). This patent states that when the number of mols of formaldehyde used "goes below 3 mol" (per mol of the hydantoin), "the yield of dimethylol-hydantoin declines precipitously and the object of the invention is not attained."

Contrary to this precaution in this Japanese patent, it was found by this invention that dimethylol-DMH can be prepared by reacting as little as from 1.85 to 2.4 mols of formaldehyde per mol of 5,5-DMH in water at a pH from 7 to about 9 for a period of about 20 minutes at a temperature from about 22° to 65° C. The invention includes also the resulting aqueous solution of dimethylol-5,5-dimethylhydantoin.

Considered broadly, the method of the invention comprises preparing an aqueous solution of dimethylol-DMH by reacting formaldehyde with DMH in the ratio of from about 1.85 to 2.4 mols of formaldehyde per mol of the 5,5-dimethylhydantoin in water at a pH of from 7 to 9 at a temperature of from about 22° to 65° C. for a time up to about 25 minutes, sufficient for the formation of the dimethylol-DMH to be substantially completed.

Optimally the formaldehyde is used in the ratio of from about 1.95 to 2.1 mols of it, and better yet at from about 1.98 to 2 mols of it, per mol of the 5,5-dimethylhydantoin; and optimally with the pH at from about 7.6 to 8.5 and better yet at from about 8.1 to 8.3; and the reaction is conducted at a temperature optimally from about 38° to 50° C. It is advantageous economically production-wise to use the formaldehyde in the form of its commercially readily available 37% aqueous solution. The 63% of water in that solution thus provides the water to serve as the reaction medium or vehicle.

As the commercial 37% formaldehyde aqueous solution generally contains various quite minor amounts of formic acid, it is desirable initially to admix in this starting formaldehyde aqueous solution sufficient of a compatible alkalizing agent to adjust the pH of the aqueous formaldehyde solution to such a level about 7 that when its reaction with the DMH is substantially complete the pH of the finished 1,3-dimethylol-DMH aqueous solution desirably will be about 7 and not exceed 7.5.

That will enable selling a substantially neutral to only slightly alkaline final product solution thereby to allow shipping the solution in drums without fear of corrosion and to avoid corrosion of the user's equipment as well as irritation to the skin of their operators working with the solution.

By "compatible alkalizing agent" is intended any commercially practical alkaline substance that does not form with the dimethylol-DMH a salt which is insoluble in the final product aqueous solution and any excess (that is over the amount used to adjust the pH) of which alkaline substance is soluble in that solution.

The reaction between the formaldehyde and the DMH is exothermic (and so also is the neutralizaton of the formic acid impurity in the commercial 37% formaldehyde aqueous solution). Thus, it is advisable to conduct the reaction in a jacketed vessel to enable maintaining the reaction within the required temperature range.

Broadly considered, the product of the invention is a substantially water-white aqueous solution containing from about 45% to about 70%, and optimally from about 50 to about 60%, of 1,3-dimethylol-5,5-dimethylhydantoin, with less than about 1.25%, and optimally under 1% of free formaldehyde and from less than 0.2% to none of unreacted DMH; and with at least 96.5% and usually at least 97.5% of the solute being 1,3-dimethylol-5,5-dimethylhydantoin.

The exceedingly low content of free formaldehyde with accompanying so high a content of the dimethylol-5,5-dimethylhydantoin in the product of the invention is a very desirable advantage over the approximately 2% of free formaldehyde and maximum of about 95% dimethylol-5,5-dimethylhydantoin (in the solute) that was obtainable by applicant's procedure prior to the process of this invention.

The method of the invention and the product provided by it are illustrated by, but not limited to, the following example:

EXAMPLE 1

5528 pouns of the commercial 37% formaldehyde aqueous solution (68.2 mols HCHO, pH3) were charged into a jacketed reaction kettle fitted with an agitator. The agitator was started and there was admixed about 2.75 pounds of 50% sodium hydroxide aqueous solution to adjust the pH of the formaldehyde solution to 8.3. Then while continuing the agitation there was admixed 4500 pounds of commercial 5,5-dimethylhydantoin (equal on dry basis to 4410 pounds, 34.45 mols; thus 1.98 mols HCHO per mol of DMH) and passing cooling water through the kettle jacket to keep the reaction mixture (heated by the exothermic reaction) temperature below 49° C. during the addition of the DMH. After the addition of the DMH was completed (the pH was 7.6), the agitation was continued while holding the reaction mixture temperature at between 39° to 49° C. for a half hour. At the end of that time the pH was between 7.5 and 7.6.

The water content of the solution was 35.8%. It is commercially desirable to market a specification-standardized solution that will remain stable in any season of the year (e.g. will not crystallize or solidify in winter). It was found that with about 45% water content the solution dependably meets that need. Accordingly, at the end of the reaction (the solution temperature was 41° C.), 1572 pounds of water were intimately admixed into the reaction product solution. Its resulting pH was 7. The solution contained 1.2% of free formaldehyde, and 98.5% of the solute was the 1,3-dimethylol-DMH.

The resulting diluted solution was cooled to 32° C. After intimately admixing into it 7 pounds of a diatomaceous filter aid, the resulting mixture was filtered and the filtered solution was filled into 55 gallon drums, ready for shipment.

The procedure such as that of the foregoing example can be repeated using the formaldehyde and the DMH in other ratios within the earlier above recited range and allowing them to react together under different operating conditions such as pH, temperature and time within their earlier above recited respective ranges to provide additional similar examples within the scope of the method and also the product of the invention.

Then also, while production-wise it is desirable to use the formaldehyde in its commercially readily available and conveniently used 37% solution in water, it can be used in its likewise available 44% or 50% solution (and with any of them inhibited with some percentage of methanol if compatible with the use to be made of the end product solution, or uninhibited) or in any of its other commercially available forms; and in any case where necessary with suitable adjustment with addition of water.

Also, when any formaldehyde solution used includes any formic acid either as impurity or stabilizing agent, or other acid as such agent, the acid can be neutralized as in the illustrative example or by use of some other alkali metal hydroxide, or potassium hydroxide, or a carbonate such as sodium carbonate or an alkaline earth hydroxide as slaked lime or even magnesium hydroxide, or any other compatible inorganic or organic alkalizing agent such as a water-soluble alkylamine or alkanolamine, as dimethyl- or diethylamine or mono-, di- or triethanolamine.

When the heat from the exothermic reaction is insufficient to raise the temperature of the reaction batch to the desired level within the range provided for conducting the reaction, a heating liquid should be passed through the jacket of the reaction vessel to provide the desired reaction temperature.

The aqueous solutions of the 1,3-dimethylol-DMH of the invention are useful, for example, as formaldehyde donors and for incorporation, as in suitably small concentrations, as a preservative in various pastes, soaps, skin creams, and liquid shampoos, and other similar preparations.

While the invention has been explained by detailed description of a specific embodiment of it, it is understood that various modifications or substitutions may be made in it within the scope of the appended claims which are intended also to cover equivalents of them.

What is claimed is:

1. The method of producing an aqueous solution of 1,3-dimethylol-5,5-dimethylhydantoin, which comprises admixing formaldehyde and 5,5-dimethylhydantoin in the ratio of from about 1.85 to 2.4 mols of formaldehyde per mol of the dimethylhydanton in water, adjusting the pH with a compatible alkalizing agent to enable conducting the reaction at a pH of at least 7 to about 9, and allowing the reactants to react at a temperature from about 22° to 65° C. and a pH from 9 to 7 for a time sufficient for the formation of the 1,3-dimethylol-5,5-dimethylhydantoin to be substantially completed.

2. The method as claimed in claim 1, wherein the formaldehyde is used in the ratio of 1.95 to 2.1 mols of it.

3. The method as claimed in claim 2, wherein the formaldehyde is used in the ratio of from about 1.98 to 2 mols of it.

4. The method as claimed in claim 2, wherein the reaction is conducted with the pH of the reaction mixture being from about 8.5 to 7.

5. The method as claimed in claim 4, wherein the pH is from about 8.3 to about 7.5.

6. The method as claimed in claim 2, wherein the reaction is conducted for from about 20 to 30 minutes.

7. The method as claimed in claim 2, wherein 1.98 to 2 mols of formaldehyde are used per mol of the dimethylhydantoin and the reaction is conducted at a pH of from 8.1 to 7.5.

8. The method as claimed in claim 1, wherein the resulting aqueous solution of the dimethylol-dimethylhydantoin has less than about 1.25% of free formaldehyde.

9. An aqueous solution of 1,3-dimethylol-5,5-dimethylhydantoin containing from about 45 to 70% of the dimethylol-dimethylhydantoin, having a maximum of 1.25% to no free formaldehyde and a pH from about 7.6 to 7, and with at least 96.5% of its solute being the dimethylol dimethylhydantoin.

10. An aqueous solution as claimed in claim 9, wherein the dimethylol-dimethylhydantoin content is about 55%.

* * * * *

UNITED STATES PATENT AND TRADEMARK OFFICE
CERTIFICATE OF CORRECTION

PATENT NO. 3,987,184

DATED October 19, 1976

INVENTOR(S) Donald Henry Foelsch

It is certified that error appears in the above-identified patent and that said Letters Patent are hereby corrected as shown below:

Column 2 line 12, "38°°" should read --38°--;

Column 2 line 22, "about" should read --above--; and

Column 3 line 3, "pouns" should read --pounds--.

Signed and Sealed this

Twenty-second Day of March 1977

[SEAL]

Attest:

RUTH C. MASON
*Attesting Officer*

C. MARSHALL DANN
*Commissioner of Patents and Trademarks*